United States Patent [19]

Baldwin et al.

[11] Patent Number: 4,609,494

[45] Date of Patent: Sep. 2, 1986

[54] 5-ACETYL-3,4,5,6-TETRAHYDRO-4-OXO-2,6-METHANO-2H-1,3,5-BENZOTHIAZOCINE(-BENZODIAZOCINE)-11-CARBOXYLATES USEFUL AS CALCIUM CHANNEL BLOCKERS

[75] Inventors: John J. Baldwin, Gwynedd Valley; David A. Claremon, Audubon; David E. McClure, Lansdale, all of Pa.

[73] Assignee: Merck & Co., Inc., Rahway, N.J.

[21] Appl. No.: 703,953

[22] Filed: Feb. 21, 1985

[51] Int. Cl.[4] .......... C07D 515/08

[52] U.S. Cl. .......... 544/250

[58] Field of Search .......... 260/243.3, 244.4, 245.7; 514/183, 248, 274

[56] References Cited

PUBLICATIONS

Hromatka et al, Chem. Abst. 69-36095y (1968).
Ehsan et al., Chem. Abst. 68-78231z (1968).
J.A.C.S. vol. 54, p. 3751 (1932), Folkers et al.
Folkers et al, JACS vol. 55, p. 3784.

*Primary Examiner*—Donald G. Daus
*Assistant Examiner*—Cecilia Shen
*Attorney, Agent, or Firm*—Salvatore C. Mitri; Michael C. Sudol

[57] ABSTRACT

Novel substituted and bridged pyrimidine compounds useful as calcium channel blockers, pharmaceutical compositions thereof, and methods of treatment are disclosed.

6 Claims, No Drawings

5-ACETYL-3,4,5,6-TETRAHYDRO-4-OXO-2,6-METHANO-2H-1,3,5-BENZOTHIAZOCINE(BENZODIAZOCINE)-11-CARBOXYLATES USEFUL AS CALCIUM CHANNEL BLOCKERS

BACKGROUND OF THE INVENTION

The pharmacological function and importance of calcium antagonists, or calcium channel blockers, is well known and has been extensively reported in the literature [see; e.g., P. D. Henry, "Comparative Pharmacology of Calcium Antagonists: Nifedipine, Verapamil and Diltiazem", *The American Journal of Cardiology,* 46, 1047–1058 (1980); K. H. Dangman, et al., "Effects of Nifedipine on Electrical Activity of Cardiac Cells", *The American Journal of Cardiology,* 46, 1061–1067 (1980); E. Braunwald, "Introduction: Calcium Channel Blockers", *The American Journal of Cardiology,* 46,1045 (1980); L. D. Hillis, "The New Coronary Vasodilators: Calcium Blockers", *J. Card. Med.,* 5(6), 583 (1980); M. J. Berridge, "Receptors and Calcium Signalling", *Trends in Pharmacological Sciences* 1, 419 , (1980); W. G. Nayler, et al., "Calcium Antagonists: definition and mode of action", *Basic Research in Cardiology,* 76, No. 1, 1–15 (1981)].

Aryl substituted pyrimidines are disclosed by K. Folkers, et al. *J. Am. Chem. Soc.* vol. 54, P. 3751 (Sept., 1932) and vol. 55, P 3784 (Sept. 1933)] and Pakistan [*J. Sci. Ind. Res.,* 10(1), 83–85 (1967) and CA, 68, 78231Z].

SUMMARY OF THE INVENTION

This invention is directed to novel substituted and bridged pyrimidines and derivatives thereof and to methods for preparing such compounds. This invention is also directed to pharmaceutical compositions and methods of treatment for cardiovascular disorders in which high cellular concentration of $Ca^{++}$ is a factor.

DETAILED DESCRIPTION OF THE INVENTION

The specific substituted and bridged pyrimidine compounds of this invention are represented by the following general structural formula (I):

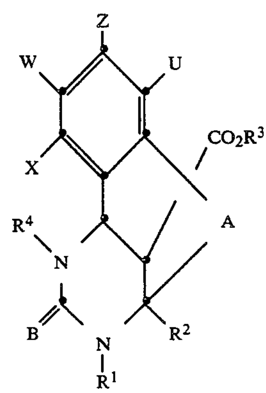

(I)

wherein:

A and B independently are oxygen or sulfur;

$R^1$ is hydrogen;

$R^2$ is hydrogen, $C_1$–$C_8$ alkyl, $C_2$–$C_8$ alkenyl, $C_3$–$C_8$ cycloalkyl, or $C_1$–$C_8$ hydroxyalkyl;

$R^3$ is $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy(alkoxyalkyl), $C_1$–$C_8$ aminoalkyl wherein the amino group is $NR^5R^6$ in which $R^5$ and $R^6$ independently are hydrogen, $C_1$–$C_8$ alkyl, $C_7$–$C_{14}$ phenylalkyl or $R^5$ and $R^6$ together with the N atom form a 5 or 6 membered heterocycle selected from the group consisting of piperidinyl, morpholinyl, pyrrolidinyl, piperazinyl, or N'—$C_1$–$C_4$-alkyl-piperazinyl;

$R^4$ is COY wherein Y is $C_1$–$C_8$ alkyl, $C_2$–$C_8$ alkenyl, $C_3$–$C_8$ cycloalkyl, $C_1$–$C_8$ alkoxy, $C_2$–$C_8$ alkenyloxy, $C_3$–$C_8$ cycloalkoxy or $NR^5R^6$ wherein $R^5$ and $R^6$ are defined above; and X, W, Z and U are independently hydrogen, $C_1$–$C_8$ alkyl, $C_1$–$C_8$ alkoxy, $C_1$–$C_8$ alkylthio, $C_1$–$C_8$ alkyl S(O), $C_1$–$C_8$ alkyl $S(O)_2$, $CF_3$, cyano, nitro, halo (fluoro, chloro and bromo) or $CONR^5R^6$ wherein $R^5$ and $R^6$ are defined above, provided that at least two of X, W, Z and U are hydrogen or X and W or W and Z or Z and U together with the phenyl group to which they are attached form a naphthyl or benzoxadiazole group, and pharmaceutically acceptable salts thereof.

The preferred compounds of this invention are those represented by the general structural formula (I) wherein:

A and B are independently oxygen or sulfur;

$R^1$ is hydrogen;

$R^2$ is hydrogen or $C_1$–$C_8$ alkyl;

$R^3$ is $C_1$–$C_8$ alkyl;

$R^4$ is COY wherein Y is $C_1$–$C_8$ alkyl or $C_1$–$C_8$ alkoxy; and

X, W, Z and U are independently hydrogen, $C_1$–$C_8$ alkoxy, $C_1$–$C_8$ alkylthio, $CF_3$, cyano, nitro or halo provided that at least two of X, W, Z and U are hydrogen.

The most preferred compounds of this invention are those preferred compounds wherein:

A is oxygen;

$R^4$ is COY wherein Y is $C_1$–$C_8$ alkyl or $C_1$–$C_8$ alkoxy; and

X, W, Z and U are independently hydrogen, $C_1$–$C_8$ alkoxy, nitro or halo provided that at least two of X, W, Z and U are hydrogen.

Illustrative of the most preferred compounds is ethyl 5-acetyl-3,4,5,6-tetrahydro-2-methyl-8-nitro-4-oxo-2,6-methano-2H-2,3,5-benzodiazocine-11-carboxylate [Formula (I) wherein A and B are oxygen, $R^1$ is hydrogen, $R^2$ is methyl, $R^3$ is ethyl, $R^4$ is acetyl, W is nitro and X, Z and U are hydrogen.]

The compounds of this invention are conveniently prepared from known or readily obtainable starting materials utilizing the general synthetic pathways described below.

The compounds of the formula (I) wherein A is oxygen are prepared as follows:

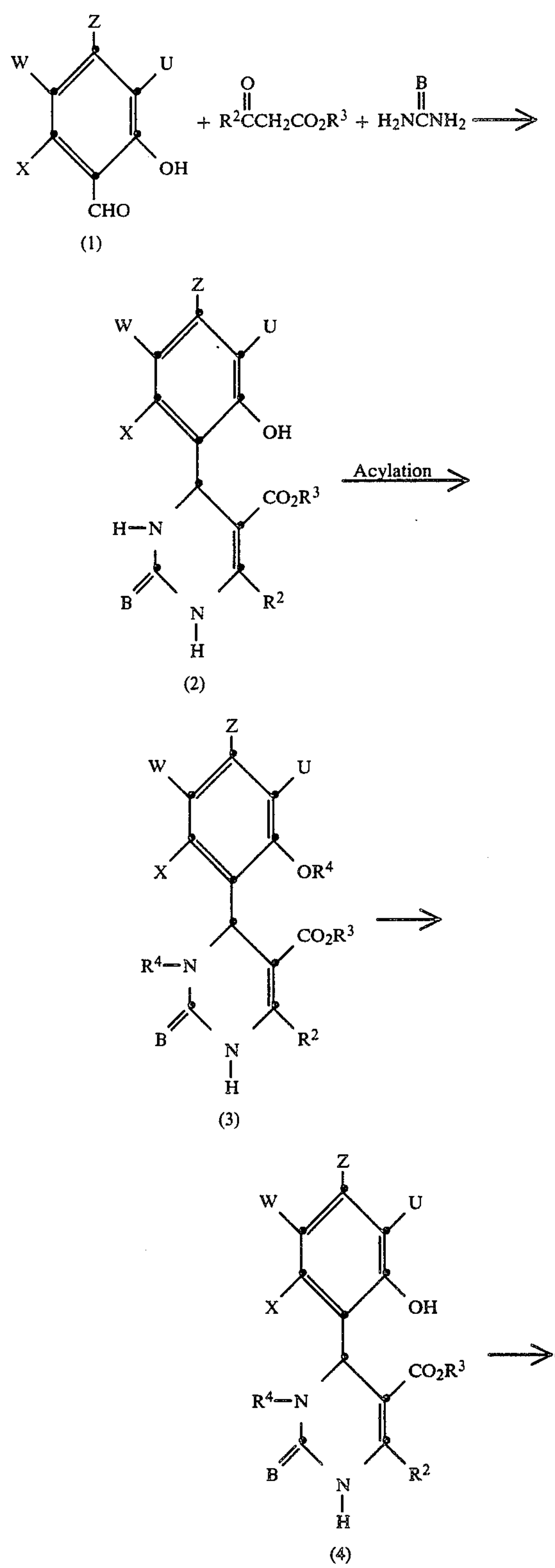

Utilizing the general procedures disclosed in the Folkers et al. or Pakistan references, the appropriately substituted 2-hydroxybenzaldehyde (1) is reacted with an appropriateldy substituted 3-oxopropanoate, such as ethyl acetoacetate, and urea or thiourea to give tetrahydropyrimidine (2). The tretrahydropyrimidine (2) is then acylated by either treatment with strong base such as methyllithium, and an acylating agent, such as methyl chloroformate or treatment with neat alkanoic acid anhydride, such as acetic anhydride at elevated temperatures to yield compound (3). The O-acyl group of compound (3) is removed under basic conditions to afford compound (4).

The compound (4) is then treated at 0° to 50° C., preferably 0° C., with between 0.01 and 0.1 equivalents, preferably 0.05 equivalents, of a strong acid in an inert solvent to give the compounds of formula (I). Examples of such strong acids include camphorsulfonic, p-toluene sulfonic, trifluoroacetic and hydrochloric acid with dl-camphorsulfonic acid being preferred. Exemplifying the inert solvents employed in this cyclization reaction are ethers, such as tetrahydrofuran, dimethoxyethane and the like, chlorinated hydrocarbons, such as chloroform, dichloromethane and the like, aromatic hydrocarbons, such as benzene, toluene and the like and polar aprotic solvents, such as acetonitrile.

The compounds of the formula (I) wherein A is sulfur are prepared as follows:

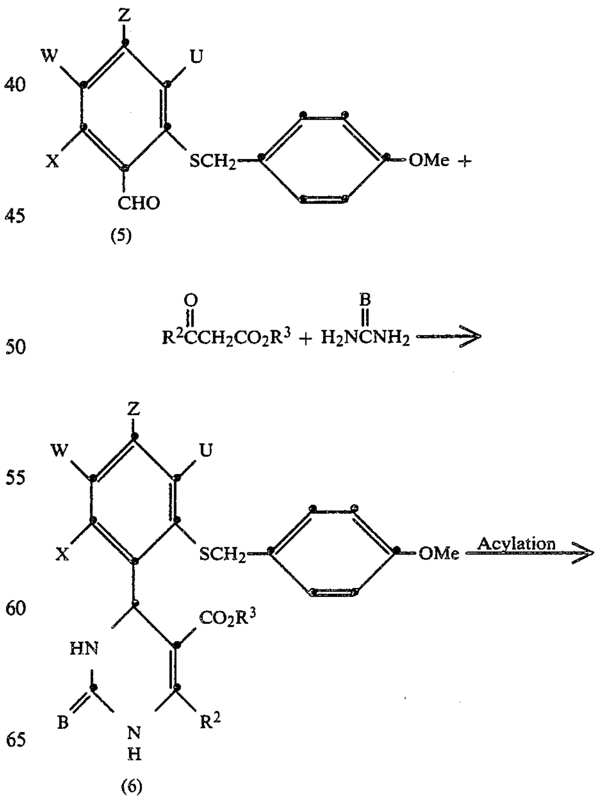

-continued

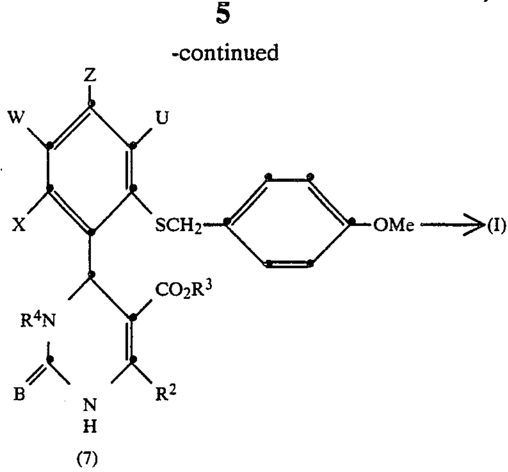

Utilizing standard procedures, the appropriately substituted 2-(p-methoxybenzylthio)benzaldehyde (5) is reacted with a 3-oxopropanoate and urea or thiourea to give the tetrahydropyrimidine (6). The tetrahydropyrimidine (6) is acylated with acetic anhydride to yield a compound (7) which is cyclized to the compounds of the formula (I) under strong acid conditions.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) are useful antihypercholesterolemic and antilipademic agents; (vii) protection of the ischemic myocardium; (viii) inhibit irritable bowel syndrome and esophageal spasm; and, (ix) inhibit migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace tritiated nitrendepine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration; e.g., as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration; e.g., dissolved or dispersed in a suitable liquid carrier or emulsified. The pharmaceutical preparations thus described are made following the conventional techniques of the pharmaceutical chemist as appropriate to the desired end product.

The ratio of active compound to compounding ingredients, i.e., carrier, diluent, etc., will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for obtaining the compounds and compositions of the invention, but are not to be construed as being limitative of the invention.

EXAMPLE 1

Preparation of Ethyl 5-acetyl-3,4,5,6-tetrahydro-2-methyl-8-nitro-4-oxo-2,6-methano-2H-1,3,5-benzodiazocine-11-carboxylate (a) Ethyl 3-acetyl-1,2,3,4-tetrahydro-4-(2-acetoxy-5-nitrophenyl)-6-methyl-2-oxo-5-pyrimidine carboxylate (1a)

A suspension of ethyl 1,2,3,4-tetrahydro-4-(2-hydroxy-5-nitrophenyl)-6-methyl-2-oxo-5-pyrimidine carboxylate (1.00 g, 31.0 mmol) in acetic anhydride (25 mL) was heated to reflux for 2 hours. The reaction mixture was cooled and the excess acetic anhydride was removed in vacuo to afford the desired product as a tan solid which was used in the next reaction without purification.

(b) Ethyl 3-acetyl-1,2,3,4-tetrahydro-4-(2-hydroxy-5-nitrophenyl)-6-methyl-2-oxo-5-pyrimidinecarboxylate (1b)

To a suspension of the Compound 1a (1.03 g) in ethanol (60 mL) at ambient temperature was added potassium carbonate (2.0 g). After stirring for 18 hours, to the reaction mixture was added saturated aqueous ammonium chloride. The reaction mixture was then extracted with methylene chloride and the combined organic extracts were dried over anhydrous sodium sulfate and filtered. The filtrate was concentrated in vacuo and the residue purified by flash chromatography on silica gel eluted with methanol:methylene chloride (3:97) to yield the desired product as a solid.

$^1$H NMR (90 MHz, $CDCl_3$/DMSO-$d_6$) δ=1.20 (t, J=7.5 Hz, 3H), 2.40 (s, 3H), 2.50 (s, 3H), 4.10 (q, J=7.5 Hz, 2H), 6.45 (s, 1H, ArC$\underline{H}$).

(c) Ethyl 5-acetyl-3,4,5,6-tetrahydro-2-methyl-8-nitro-4-oxo-2,6-methano-2H-1,3,5-benzodiazocine-11-carboxylate The compound 1b (150 mg) was dissolved in chloroform and then treated with dl-camphorsulfonic acid (2 mg) at 50° C. for 48 hours. The reaction mixture was cooled to ambient temperature, diluted with chloroform, washed with water, dried over anhydrous sodium sulfate, and filtered. The filtrated was concentrated in vacuo and the residue purified by flash chromatography on silica gel eluted with methanol: methylene chloride (5:995) and recrystallization from diethyl ether:hexane (1:1) to yield the desired product as a mixture of dl pairs of diastereomers.

$^1$H NMR (360 MHz, DMSO-$d_6$) δ=6.03 (d, J=3.0 Hz, 1H, ArC$\underline{H}$-CHCO$_2$Et) and δ=6.16 (d, J=3.0 Hz, 1H, ArCH-C$\underline{H}$CO$_2$Et).

The mixture of dl pairs of diastereomers can be separated by high pressure liquid chromatography (HPLC).

EXAMPLE 2

Preparation of Ethyl 5-acetyl-3,4,5,6-tetrahydro-2-methyl-8-nitro-4-oxo-2,6-methano-2H-1,3,5,-benzothiadiazocine-11-carboxylate (a) Ethyl 1,2,3,4-tetrahydro-4-(2-(p-methoxybenzylthio)-5-nitrophenyl)-6-methyl-2-oxo-5-pyrimidine carboxylate (2a)

A mxiture of 5-nitro-2-(p-methoxybenzylthio)benzaldehyde (1.0 mmol), urea (1.5 mmol) and ethyl acetoacetate (1.5 mmol) in ethanol (2 ml) is heated with a catalytic amount of hydrochloric acid to yield the compound 2a.

(b) Ethyl 3-acetyl-1,2,3,4-tetrahydro-4-(2-(p-methoxybenzylthio)-5-nitrophenyl)-6-methyl-2-oxo-5-pyrimidine carboxylate (2b)

The compound 2a is treated with excess acetic anhydride and is heated to reflux for 2 hours to yield the compound 2b.

(c) Ethyl 5-acetyl-3,4,5,6-tetrahydro-2-methyl-8-nitro-4-oxo-2,6-methano-2H-1,3,5-benzothiadiazocine-11-carboxylate The compound 2b is treated with anhydrous trifluoroacetic acid:anisole (1:1) at 25° C. for 1 hour to yield a mixture of the diastereomers of the desired product. The individual diastereomers may be separated by chromatography.

EXAMPLES 3-9

The following compounds of the formula (I) wherein A is oxygen and R$^1$ is hydrogen are prepared from the appropriately substituted dihydropyridine compound utilizing the general procedures of Example 1.

| Compound No. | B | R$^2$ | R$^3$ | R$^4$ | U | Z | W | U |
|---|---|---|---|---|---|---|---|---|
| 3 | O | Me | Me | $-COCH_3$ | H | H | H | H |
| 4 | O | Et | Et | $-CO_2CH_3$ | H | OMe | H | H |
| 5 | O | H | $-CH_2-CH=CH_2$ | $-COCH_3$ | H | SMe | H | H |
| 6 | O | $-CH_2CH_2OH$ | $-CH_2CH_2N(CH_2Ph)CH_3$ | $-CO_2CH_3$ | H | H | $CF_3$ | H |
| 7 | S | Me | Me | $-COCH_3$ | H | $-CN$ | H | H |
| 8 | S | $-CH_2CH_2OCH_3$ | Et | $-CO_2CH_3$ | H | H | H | H |
| 9 | S | Me | Et | $-COCH_3$ | H | H | H | H |

EXAMPLE 10

As a specific embodiment of a composition of this invention an active ingredient, such as ethyl 5-acetyl-3,4,5,6-tetrahydro-2-methyl-8-nitro-4-oxo-2,6-methano-2H-1,3,5-benzodiazocine-11-carboxylate, is formulated to yield 5000 compressed tablets, each containing 50 mg of the active ingredient, as follows:

| | |
|---|---|
| Active ingredient | 250 grams |
| Starch | 70 grams |
| Dibasic calcium phosphate hydrous | 500 grams |
| Calcium stearate | 2.5 grams |

What is claimed is:

1. A compound represented by the following structural formula (I):

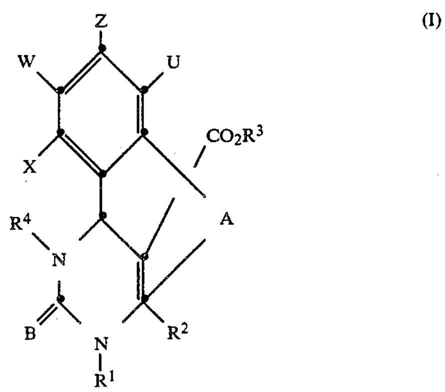

wherein:

A and B are independently oxygen or sulfur;

R$^1$ is hydrogen;

$R^2$ is hydrogen, $C_1$–$C_8$ alkyl, $C_2$–$C_8$ alkenyl, $C_3$–$C_8$ cycloalkyl, or $C_1$–$C_8$ hydroxyalkyl;

$R^3$ is $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy(alkoxyalkyl), $C_1$–$C_8$ aminoalkyl wherein the amino group is $NR^5R^6$ in which $R^5$ and $R^6$ independently are hydrogen, $C_1$–$C_8$ alkyl, $C_7$–$C_{14}$ phenylalkyl;

$R^4$ is COY wherein Y is $C_1$–$C_8$ alkyl, $C_2$–$C_8$ alkenyl, $C_3$–$C_8$ cycloalkyl, $C_1$–$C_8$ alkoxy, $C_2$–$C_8$ alkenyloxy, $C_3$–$C_8$ cycloalkoxy or $NR^5R^6$wherein $R^5$ and $R^6$ are defined above; and X, W, Z and U are independently hydrogen, $C_1$–$C_8$ alkyl, $C_1$–$C_8$ alkoxy, $C_1$–$C_8$ alkylthio, $C_1$–$C_8$ alkyl S(O), $C_1$–$C_8$ alkyl $S(O)_2$, $CF_3$, cyano, nitro, halo or $CONR^5R^6$ wherein $R^5$ and $R^6$ are defined above, provided that at least two of X, W, Z and U are hydrogen or X and W or W and Z or Z and U together with the phenyl group to which they are attached form a naphthyl or benzoxadiazole group, or a pharmaceutically acceptable salt thereof.

2. A compound according to claim 1 wherein:

$R^2$ is hydrogen or $C_1$–$C_8$ alkyl;

$R^3$ is $C_1$–$C_8$ alkyl;

$R^4$ is COY wherein Y is $C_1$–$C_8$ alkyl or $C_1$–$C_8$ alkoxy; and

X, W, Z and U are independently hydrogen, $C_1$–$C_8$ alkoxy, $C_1$–$C_8$ alkylthio, $CF_3$, cyano, nitro or halo provided that at least two of X, W, Z and U are hydrogen.

3. A compound according to claim 2 wherein:

A is oxygen;

$R^4$ is COY wherein Y is $C_1$–$C_8$ alkyl or $C_1$–$C_8$ alkoxy; and

X, W, Z and U are independently hydrogen, $C_1$–$C_8$ alkoxy, nitro or halo provided that at least two of X, W, Z and U are hydrogen.

4. A compound according to claim 3 which is ethyl 5-acetyl-3,4,5,6-tetrahydro-2-methyl-8-nitro-4-oxo-2,6-methano-2H-1,3,5-benzodiazocine-11-carboxylate.

5. A pharmaceutical composition, useful in the treatment of cardiovascular disorders, comprising a nontoxic therapeutically effective amount of a compound according to claim 1 in an admixture with a pharmaceutically acceptable carrier.

6. A method of treatment for cardiovascular disorders which comprises administering to a subject in need of such treatment a nontoxic therapeutically effective amount of a compound according to claim 1.

* * * * *